United States Patent [19]

Carman

[11] Patent Number: 5,365,429
[45] Date of Patent: Nov. 15, 1994

[54] COMPUTER DETECTION OF MICROCALCIFICATIONS IN MAMMOGRAMS

[75] Inventor: Charles S. Carman, Ossining, N.Y.

[73] Assignee: North American Philips Corporation, New York, N.Y.

[21] Appl. No.: 3,071

[22] Filed: Jan. 11, 1993

[51] Int. Cl.$^5$ .......................... G06F 15/00; A61B 6/04
[52] U.S. Cl. ........................... 364/413.13; 364/413.15; 378/37
[58] Field of Search ...................... 364/413.15, 413.13, 364/413.26, 413.22, 413.14; 382/6; 378/37; 128/754; 250/341

[56] References Cited

U.S. PATENT DOCUMENTS

| | | | |
|---|---|---|---|
| 4,515,165 | 5/1985 | Carroll | 128/664 |
| 4,618,990 | 10/1986 | Sieb, Jr. et al. | 382/43 |
| 4,851,984 | 7/1989 | Doi et al. | 364/413.23 |
| 4,907,156 | 3/1990 | Doi et al. | 364/413.13 |
| 5,003,979 | 4/1991 | Merickel et al. | 364/413.13 |
| 5,142,557 | 8/1992 | Toker et al. | 378/37 |
| 5,212,637 | 5/1993 | Saxana | 364/413.26 |

FOREIGN PATENT DOCUMENTS

| | | |
|---|---|---|
| 2622714 | 5/1989 | France . |
| 9107135 | 5/1991 | WIPO . |

OTHER PUBLICATIONS

"Image Processing for Recognition of Tumor on Mammography", S. Yabashi et al, Proceedings of the 1989 International Symposium on Noise and Cluster Rejection in Radars and Imaging Sensors, IEICE 1989.

Philippe Saint-Marc et al, "Adaptive Smoothing: A General Tool for Early Vision", IEEE Transactions on Pattern Analysis and Machine Intelligence, vol. 13, No. 6, Jun. 1991, pp. 514–529.

Joachim Dengler et al, "Segmentation of Microcalcifications in Mammograms", submitted to IEEE Transactions on Medical Imaging, 1991.

Petros Maragos et al, "Morphological Systems for Multidimensional Signal Processing", Proceedings of the IEEE, vol. 78, No. 4, Apr. 1990, pp. 690–710.

Anil K. Jain, et al, "Algorithms for Clusterming Data", Chapter 3, pp. 72–80 Prentice Hall, Englewood Cliffs, N.J. 1988.

Raj Jain, "The Art of Computer Systems Performance Analysis-Techniques for Experimental Design, Measurement, Simulation, and Modeling", pp. 192–197, John Wiley & Sons, New York, 1991.

Laurens V. Ackerman et al, "Breast Lesion Classification by Computer and Xeroradiograph", Cancer, vol. 30, pp. 1025–1035, Oct. 1972.

(List continued on next page.)

Primary Examiner—Roy N. Envall, Jr.
Assistant Examiner—Khai Tran
Attorney, Agent, or Firm—Jack D. Slobod

[57] ABSTRACT

A method of aiding detection of breast cancer by computer analysis of a mammogram image includes computing filtered second spatial derivative of intensity values at the pixels of the image, in the form of a Laplacian. The filtering is iterative adaptive smoothing of the first spatial derivative, which smoothing is applied to achieve relatively great smoothing effect where there is relatively little local variation in derivative value and a relatively small or no smoothing effect where there is relatively great local variation in derivative value. This has the effect of preserving locations of zero crossings in the Laplacian which correspond to edges or boundaries in the image. Regions of negative Laplacian value are labelled and connected. These labelled regions are locally bright spots in the image. From the preserved boundary locations of these locally bright spots, a plurality of feature measures are computed, indicative of their respective brightnesses, shapes and edge contrasts. Those locally bright spots having a weighted combination of logarithms of these feature measures exceeding a predetermined value are identified as microcalcifications of a type associated with cancer, and it is detected where such identified microcalcifications are grouped in clusters.

4 Claims, 5 Drawing Sheets

OTHER PUBLICATIONS

Heang-Ping Chan et al, "Computer Aided Detection of Microcalcifications in Mammograms-Methodology and Preliminary Clinical Study", Investigative Radiology, vol. 23, pp. 664–671, Sep. 1988.

D. H. Davies et al, "Automatic Detection of Microcalcifications in Digital Mammograms Using Local Area Thresholding Techniques", Medical Imaging III: Image Processing, vol. 1092, pp. 153–159, SPIE, 1989.

Hahaa W. Fam et al, "The Detection of Calcification Clusters in Film-Screen Mammograms; A Detailed Algorithmic Approach", Medical Imaging II, vol. 914, pp. 620–634, SPIE, 1988.

Stanley H. Fox et al, "A Computer Analysis of Mammographic Microcalcifications: Global Approach", pp. 624–631, IEEE 1980, Proceedings of the 5th International Conf. on Pattern Recognition.

Nico Karssemeijer, "A Stochastic Method for Automated Detection of Microcalcifications in Digital Mammograms", submitted to XIIth Conf. on Inf. Proc. in Med. Imaging, pp. 1–14, Jul. 1991.

Wolfgang Spiesberger, "Mammogram Inspection by Computer" IEEE Transactions on Biomedical Engineering, vol. BME 26, No. 4, Apr. 1979, pp. 213–219.

William G. Wee et al, "Evaluation of Mammographic Calcifications Using a Computer Programs", Radiology, vol. 116, pp. 717–720, Sep. 1975.

Bahaa W. Fam et al, "Algorithm for the Detection of Fine Clustered Calcifications on Film Mammograms", Radiology, vol. 169, pp. 333–337, Nov. 1988.

D. H. Davies et al, "Automatic Computer Detection of Clustered Calcifications in Digital Mammograms", Phys. Med. Biol. vol. 35, No. 8, 1112–1118, 1990.

Heang-Ping Chan et al, "Image Feature Analysis and Computer Aided Diagnosis in Digital Radiography", Medical Physics, vol. 14, No. 4, pp. 538–548, Jul. 1987.

Anil K. Jain, "Fundamentals of Digital Image Processing", Chapter 9, pp. 347–357, Prentice-Hall, Englewood Cliff, N.J., 1989.

Atam P. Dhawan et al, "Mammographic Feature Enhancement by Computerized Image Processing", Computer Methods and Programs in Biomedicine, vol. 27, pp. 23–35, 1988.

Isaac N. Bankman et al, "Automated Defection of Microcalcification Clusters in Mammograms", in S/CAR 90: Comp. App. to Assist Radiology, pp. 137–143, Symposia Foundation, Carlsbad, Calif. 1992.

COMPUTER DETECTION OF MICROCALCIFICATIONS IN MAMMOGRAMS

BACKGROUND OF THE INVENTION

1. Field of the Invention

The present invention relates generally to methods for aiding in the detection of cancer by utilizing computer analysis of radiologic images to identify spots corresponding to objects associated with malignancy. In its more particular respects, it relates to methods of aiding in the detection of breast cancer by computer identification of microcalcifications and clusters thereof in mammographic images.

2. Description of the Related Art

Breast cancer is one of the primary causes of death for women in western societies. Because the vast majority of deaths due to cancer that originated in the breast could be prevented by early detection, several national health organizations in the United States now recommend that all women over the age of 40 have regular screening mammograms. In fact, the National Cancer Institute has set a goal of 80% compliance by the end of the decade. To reach this goal, the number of mammograms taken and read in the U.S. would have to double, and in some localities, more than triple. An increase of this magnitude would overload the current capacity to take and interpret mammograms.

The reading or interpretation of screening mammograms is an art that requires extensive experience and attentiveness to detail. While the radiologist's primary sign for cancer is a mass visible on the mammogram, one of the more sensitive signs is the presence of small relatively bright spots (in film-screen mammography) corresponding to locally increased X-ray attenuation due to minute (<5 mm in maximum dimension in the film image) deposits of calcium salts known as microcalcifications, each generally of irregular shape, and which are arranged in clusters. In fact, clustered microcalcifications are often the only sign indicating an early in situ malignancy. Unfortunately, these small spots generally appear in the images as obscured by gradations in background produced by surrounding tissue and their visibility is limited by the image's resolution, contrast and signal to noise ratio. Consequently, the probability of their detection by an experienced radiologist is not as high as desirable, making double independent readings a common practice to achieve acceptable results.

A method of computer identification of microcalcifications in digitized mammogram images is known from U.S. Pat. No. 4,907,156, which method is also applicable to a related problem of detection of spots in digitized chest X-ray images corresponding to lung nodules. Therein, spatial filtering was employed to deemphasize both low and very high spatial frequencies in the image attempting to increase the conspicuity of the microcalcifications. In particular, a difference image was formed of the results of application to the original image of a filter matched to a particular spot size and a median filter. An adaptive thresholding technique was used to label spots as calcifications, which spots also had to meet defined shape characteristics.

Accurate measurements of area, perimeter and shape of a spot are critical in classifying whether or not it corresponds to a microcalcification of a type associated with malignancy. Yet, prior art methods applied to make spots more conspicuous in radiologic images, such as that above-described, generally fail to preserve the locations of the edges or boundaries of the spots. Global spatial filtering with, for example, a Gaussian shaped filter, tends to smear these edges.

The problem of preservation of size and shape was addressed in J. Dengler et al. "Segmentation of Microcalcifications in Mammograms", (citation presently unknown). Therein, Gaussian high pass spatial filtering was used to remove the low frequency structural noise and "Difference of Gaussian" (DOG) spatial filtering was used to locate bright spots within a small range of sizes. Because this processing smoothed the boundaries of the spots, a morphological filter known as a "top-hat" transformation was applied to the original image to attempt to extract the boundaries of the spots. The spots located by the DoG filtering were iteratively expanded in size by topologically unimportant pixels, although not beyond the spot boundaries given by the morphological filter operation.

The efficacy of the method of J. Dengler et al. is dependent on proper choices for various spatial filter parameters (including positive and negative kernel widths, weight and threshold for the DoG filtering) which generally determine a range of sizes of spots that are detected as microcalcifications. Because of the irregular and frequently elongated nature of the microcalcification shapes of interest, it is not believed advisable to employ a size selective spatial filter which significantly restricts the range of spot sizes detected, particularly in a manner which is substantially independent of their shape. Further it does not seem wise to select candidate microcalcifications by thresholding intensity values. Such criteria may fail to select relatively dull spots which nonetheless have sharp edges.

Edge extraction is important in the general field of computer vision. An algorithm is discussed in P. Saint-Marc et al., "Adaptive Smoothing: A General Tool for Early Vision" IEEE Transactions on Pattern Analysis and Machine Intelligence, Vol. 13, No. 6, pp. 514–529, 1991, which tends to maintain edge definition in filtered range images.

SUMMARY OF THE INVENTION

It is an object of the present invention to provide a method of aiding detection of cancer by utilizing computer detection of spots in digitized mammogram radiologic images in a manner which is not significantly dependent on the size of the spots and which preserves the locations of their edges or boundaries, from which edge locations, the spots are characterized by the computer as to whether they correspond to objects, in particular microcalcifications, of shape, edge contrast, brightness, and arrangement associated with malignancy. It is a further object of the present invention that such method involve a minimum number of parameters, which are where possible, computed from the image.

Briefly, these objects are satisfied by, with respect to a generated mammogram image stored in a digital storage device or medium accessible to a computer, computing filtered second spatial derivative of intensity values at the pixels of the image, in the form of a Laplacian, the zero crossings of which indicate edges. Regions of negative Laplacian value (which are therefore on the locally brighter side of the edges) are labelled and connected as locally bright spots. A plurality of feature measures are computed indicative of the respective shapes, edge contrasts and brightnesses of these locally bright spots, and a weighted combination of these feature measures is used to identify those spots corresponding to microcalcifications of a type associated with cancer. Thereafter, it is detected where the spots identified as microcalcifications are arranged in clusters, and the location of such clusters in the image are displayed on a monitor, or in some other human intelligible form.

The Laplacian values are determined in a manner that preserves the locations of edges. In particular, first spatial derivative of intensity values in the X and Y directions (i.e. gradient component values) are computed for each pixel position. Then, the first spatial derivative values in the X and Y directions are adaptive filtered by an iterative "adaptive smoothing" technique where in each iteration the strength or weakness of smoothing applied at each point in the image is determined from local conditions. In particular, measures of dispersion of differences between values of the first spatial derivative at adjoining pixel positions in the X and Y directions for the entire image are formed and smoothing applied to first spatial derivative values in the X and Y directions more strongly where there is little local variation in value relative to the respective dispersion measures, and more weakly where there is relatively great local variation. Values of the spatial derivative of the adaptively smoothed first derivative in X and Y directions are computed for each pixel position in the same respective directions to form second spatial derivative of intensity values in the X and Y directions. The Laplacian value is determined for each pixel position by adding the second spatial derivative values in the X and Y directions.

Other objects, features and advantages of the present invention will become apparent upon perusal of the following detailed description when taken in conjunction with the appended drawing, wherein:

DETAILED DESCRIPTION OF THE PREFERRED EMBODIMENTS

Figure 1:
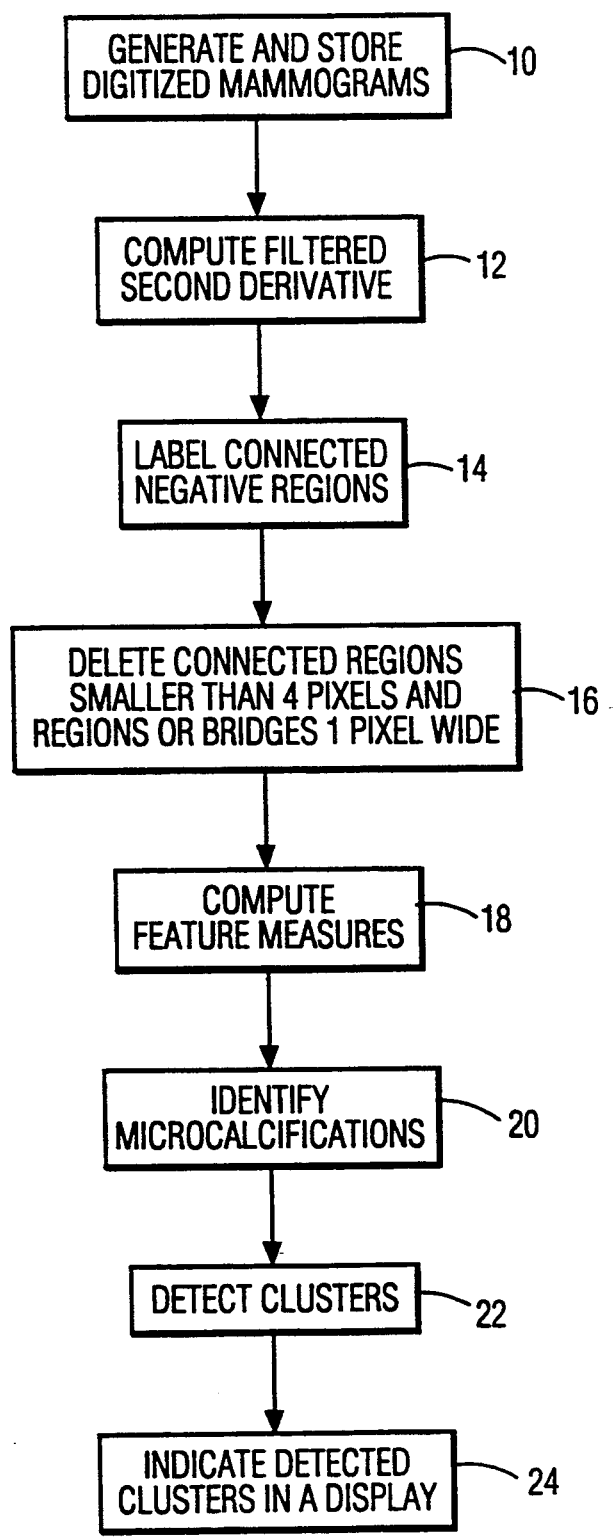
FIG. 1 is a basic flow chart of the method of the present invention.

Digitized images are readily available from imaging applications where X-ray image intensifier/camera chain or fluorescent image plate/laser readout or selenium plate/electrometer readout technologies are employed, without the necessity of scanning film. Such technologies are progressing in their spatial resolution and contrast sensitivities achieved and may soon find widespread use for mammographic applications. Presently, however, X-ray images of the human breast are generally obtained with film-screen technology. Based on studies by others of the resolution needed to properly represent individual microcalcifications in mammograms, available film scanners having spatial resolution of no worse than 0.1 mm per pixel and intensity amplitude resolution of at least 10 (and preferably 12) bits per pixel are required to produce a digitized image suitable for the purposes of the present invention. As shown in FIG. 1 of the drawing, the generation of the digitized X-ray image and its storage, for example as an image data file, on a suitable machine readable medium accessible to a computer workstation (not shown) such as a hard disk or RAM memory (not shown) forms the first step 10 in the method of the present invention. The computer workstation accesses the stored image information and performs various operations thereon, in the nature of image processing, in order to identify microcalcifications, and in particular to indicate clusters thereof. Such identification will aid early detection of breast cancer and could be used in a variety of operational modes as its efficacy is verified. Improving detection sufficiently to obviate the present practice of double reading would free significant radiologist reading resources.

As previously noted, the detection of microcalcifications of a type associated with malignancy requires significant experience. The important and most commonly noted characteristics of microcalcifications of this type are that they are relatively bright spots (in film-screen mammography) usually irregular in shape, e.g. elongated, and/or pointed, have sharp edge contrast with their surrounds, and most importantly, occur in clusters of at least 3 to 5 per square cm. in the radiologic film image. The irregular nature of these microcalcifications of interest indicate that it is crucial to preserve the location of edges in the identified spots so that suitable feature measures for classifying the spot can be accurately determined.

The Laplacian Of a Gaussian (LOG) is a widely published example of a filtered second spatial derivative operator. The technique of using the Zero Crossings of the Filtered Second Derivative (ZCFSD) for detecting and locating edges is based on a significant body of theoretical literature. The filtering, which is low pass, is designed to decrease the noise in the second derivative. Traditionally as in the LOG, the filter is Gaussian. As previously noted, such global spatial filtering has the disadvantage of moving edges away from their actual location in the image. I have employed a filtered second derivative which is produced in a manner that its zero crossings are located at edges in the image.

Figure 4A:
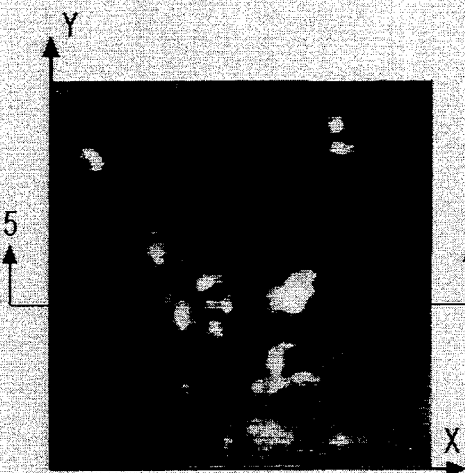
FIGS. 4a through 4f are exemplary 2 D images displaying pixel values at various stages of image processing in accordance with the flow chart of FIG. 1, wherein, for the purpose of display, the intensities of the pixels of the images of FIGS. 4b through 4e are produced by adding a positive bias to their bipolar values equal to the largest negative value, so that a large negative value for a pixel appears as black.
Figure 4B:
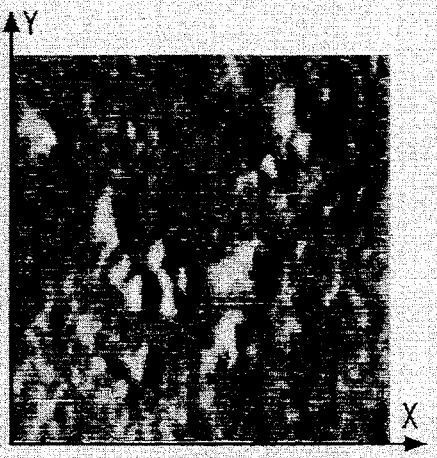
Figure 4C:
Figure 4D:
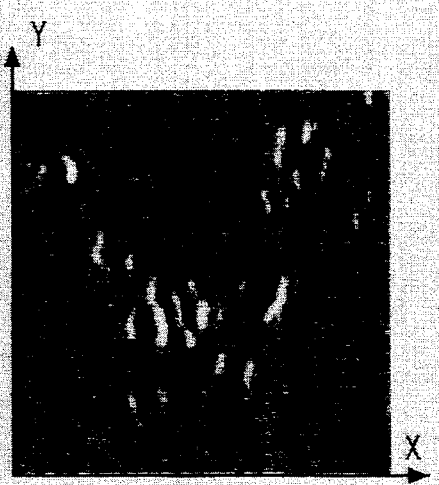
Figure 4E:
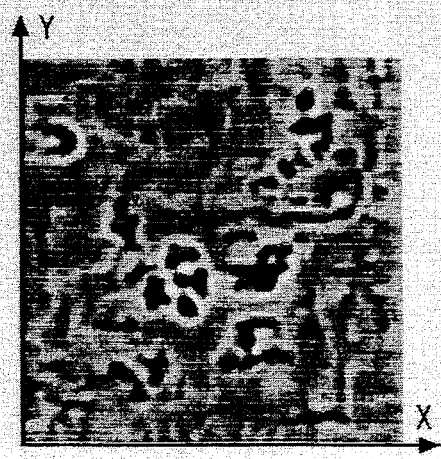
Figure 4F:
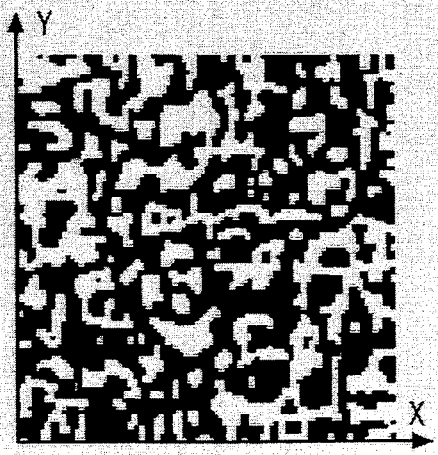
Figure 5A:
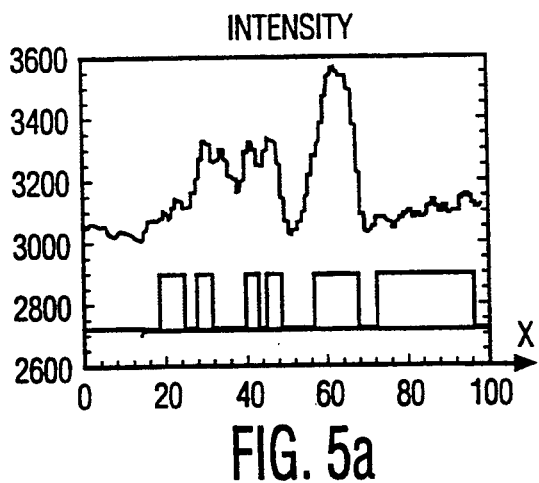
FIGS. 5a through 5f are exemplary graphs of pixel value versus position along a horizontal line 5—5 in FIG. 4a at the same stages of image processing as indicated in FIGS. 4a through 4f, respectively. The graph of FIG. 5f also appears in FIG. 5a as an aid in correlating between them.
Figure 5B:
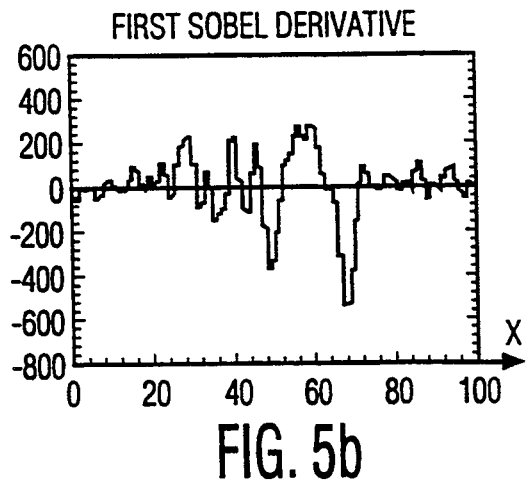
Figure 5C:
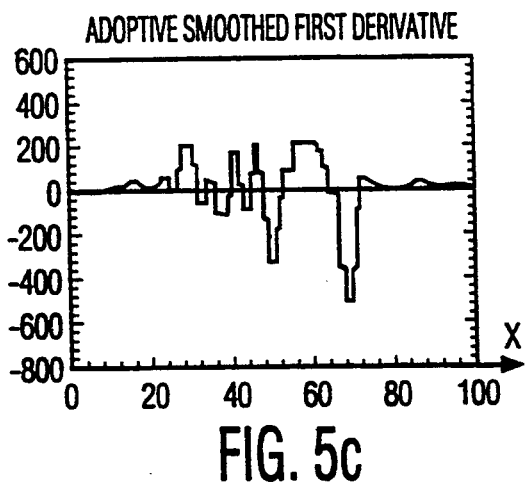
Figure 5D:
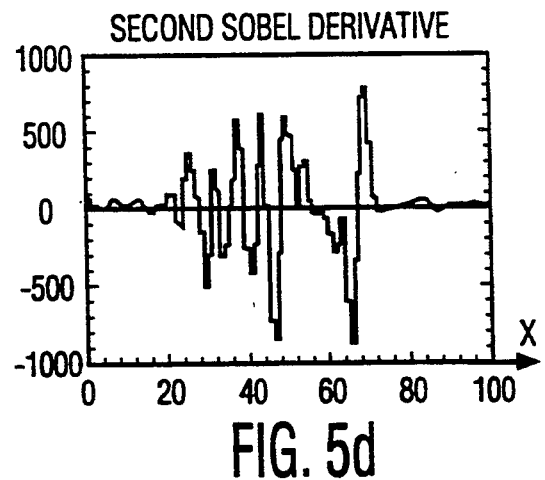
Figure 5E:
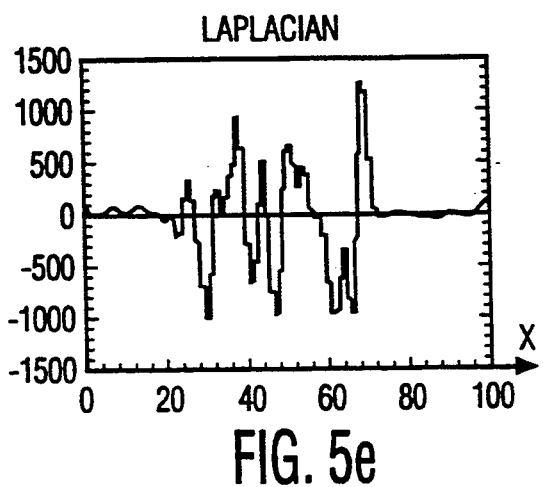
Figure 5F:
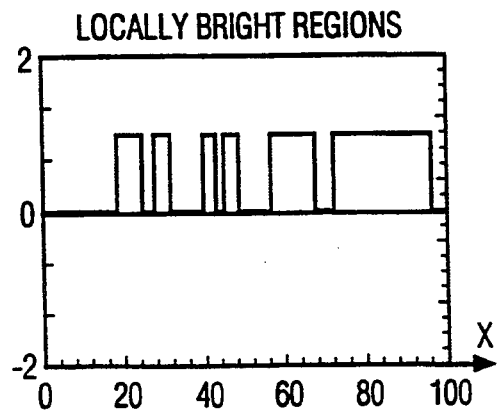

An overview of the present inventive method is apparent from the basic flow chart of FIG. 1. Therein, the original radiologic image generated and stored in box or step 10, which image comprises a rectangular array of pixels having respective intensities at each pixel position, is accessible for further processing. An example of a portion of an actual image is shown in FIG. 4a and of the intensities along a horizontal line therethrough in Figure 5a. The filtered second derivative thereof, in the form of a Laplacian, is computed in box 12, in a manner preserving the edge locations as zero crossings and connected regions of negative second derivative proximate the zero crossings are labelled by box 14. It may be recognized from examination of FIGS. 4e and 5e that regions of negative second derivative (which are black in FIG. 4e) next to a zero crossing are on the bright side of an edge in the original image. The output of box 14 is a mask as shown in FIGS. 4f and 5f wherein locally bright regions or spots are white and the balance of the mask is black. Thereafter, in box 16, regions labelled by box 14 that are smaller than four pixels are deleted or removed from further consideration as candidates for microcalcifications of interest, by for example being set to black in the mask of locally bright regions. Similarly, labelled regions or bridges between portions of labelled regions which are only one pixel in width are deleted. Any regions split thereby are separately labelled. In box 18, feature measures are computed from the edge locations of the remaining locally bright spots. These feature measures are used in box 20 to identify or detect those of the locally bright spots which correspond to micro-calcifications of interest. Clusters containing at least three such microcalcifications in a square cm. are identified or detected in box 22. In box 24, these clusters are indicated by the computer in a human intelligible manner, e.g. on a CRT display (not shown) of the original image by circling, brightening or coloring the detected clusters on the display, thereby rendering them conspicuous. The procedures in the foregoing overview will now be explained in more detail.

Figure 2:
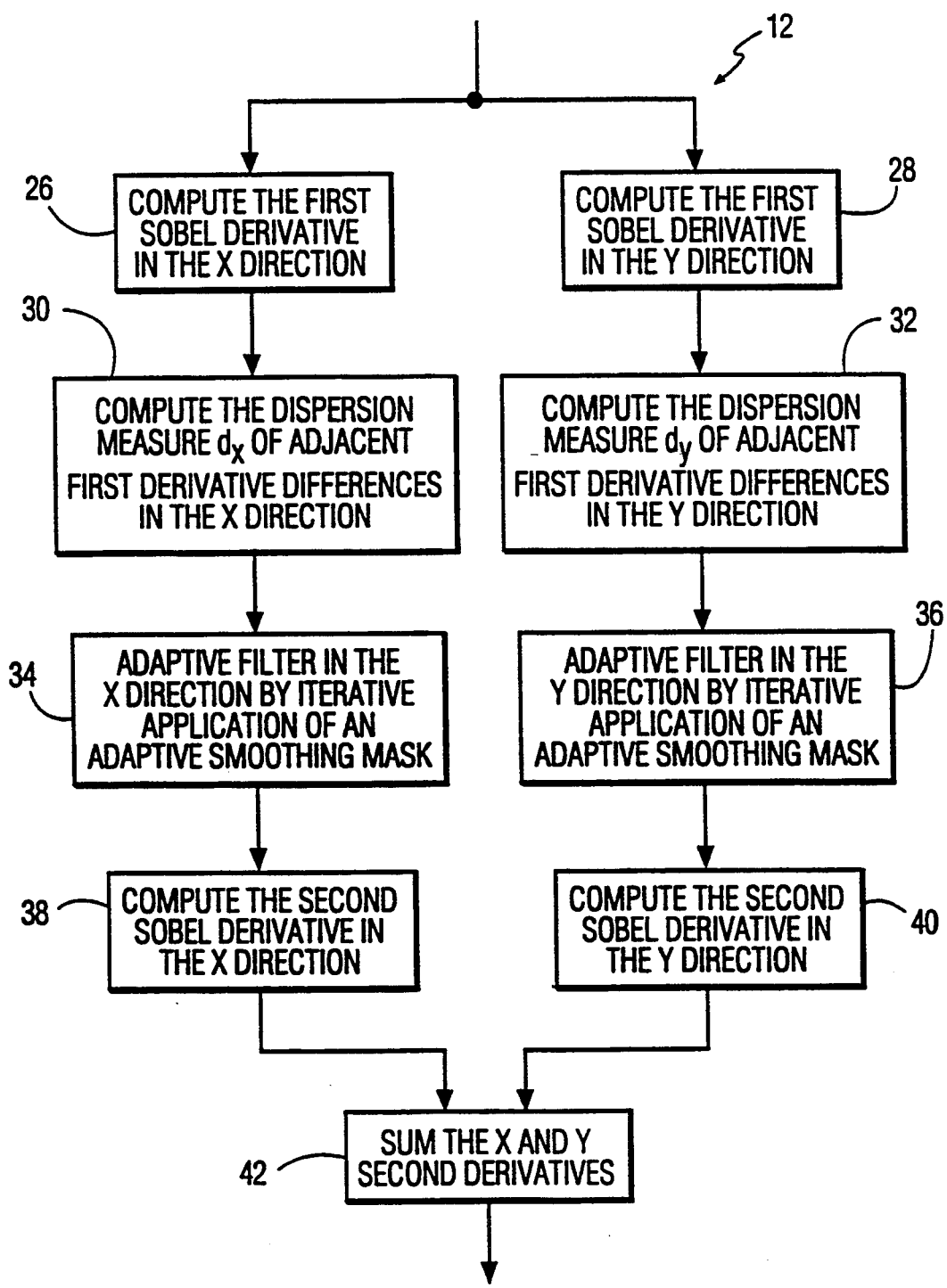
FIG. 2 is a flow chart of the detail of a filtered second derivative computation block in FIG. 1.

The detail of the computation of the filtered second derivative is shown in FIG. 2. Therein, the first spatial derivatives of the original intensity image are computed in boxes 26 and 28 for the respective X and Y directions. The exemplary result of computation of the first spatial derivative in the X direction is shown in FIGS. 4b and 5b. These computations are made using the well known Sobel 3×3 gradient operators. Measures of the dispersions $d_x$ and $d_y$ of differences between first derivative values at adjoining pixel positions throughout the image in respective X and Y directions are determined in respective boxes 30 and 32. The first spatial derivatives in the X and Y directions are adaptive filtered in these directions by boxes 34 and 36, using an iterative adaptive smoothing, that adaptively smooths (in each iteration, convolves with a small averaging mask or kernel having locally adapted weights) first derivative values in the X and Y directions in a manner that there is relatively great smoothing applied where local variation in derivative values relative to the respective measures of dispersion $d_x$ and $d_y$ in these directions. In particular, a 3×3 averaging mask is used whose central relative weight to be applied to the first derivative value $FD_O$ at the considered pixel position is unity and whose other eight relative weights to be applied to first derivatives $FD_S$ at surrounding pixel positions touching the considered pixel position by a pixel side or corner is:

$$\exp-((FD_S-FD_O)/d)^2$$

where d is respectively $d_x$ and $d_y$ for smoothing operations in the respective X and Y directions. I have found experimentally that, in blocks 30 and 32, computing the dispersions $d_x$ and $d_y$ as one half the range of the central third of the population of first derivative differences between adjoining pixel positions in the respective X and Y directions over the entire image, produces good results in combination with 9 iterations of application of the adaptive smoothing mask in boxes 34 and 36. The result of iterative adaptive smoothing the first spatial derivative of intensity in the X-direction for the exemplary image portion is shown in FIGS. 4c and 5c.

Spatial derivatives are computed in boxes 38 and 40 in respective X and Y directions of the adaptive filtered first spatial derivative of intensity values determined in boxes 34 and 36 to form filtered second derivative values in respective X and Y directions. FIGS. 4d and 5d illustrate the result of taking the spatial derivative in the X direction of the adaptive filtered first spatial derivative in the X direction. These spatial derivatives or gradients use the Sobel gradient operators. The filtered second spatial derivative values in the respective X and Y directions are added in box 42 to form a Laplacian value at each pixel position. The Laplacian is illustrated in FIGS. 4e and 5e for the exemplary image portion.

Figure 3:
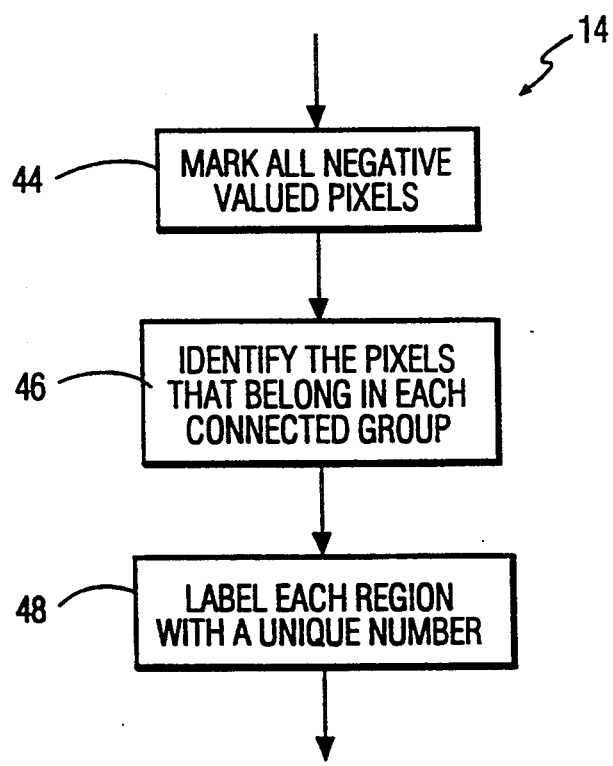
FIG. 3 is a flow chart of the detail of a connected negative region labelling block in FIG. 1.

The boundaries of spots are determined from connected regions of negative Laplacian value. These are labelled in accordance with the flow chart of FIG. 3. In particular, in box 44, all pixel positions having negative Laplacian values are marked by a thresholding operation at the value zero. Those pixel positions having a Laplacian of less than zero are assigned a white value and those having non-negative Laplacian values are assigned a black value. In block 46, the interiors of marked connected regions of pixels (closed contours) are filled with white values. Each connected region is assigned a unique associated number in block 48. Block 16 then deletes regions smaller than four pixels and one pixel wide regions or bridges from further consideration, by for example, assigning the deleted regions or pixels to the black level. There results a mask of candidate locally bright regions or spots as illustrated in FIGS. 5f and 6f for the exemplary image portion.

For the purpose of discrimination of spots corresponding to mirocalcifications, I assume that microcalcifications are brighter than their surround, tend to have a compact shape, and they tend to have high edge gradients. It is true, however, that some microcalcifications of interest may appear to violate the assumption of compactness. However, this measure has been included to discriminate microcalcifications from scratches in the film and many fibrous objects such as ducts, blood vessels and support fibers.

Hence, in block 20, several measures are computed on the mask of locally bright regions or spots and their surrounding pixels which are indicative of the aforementioned characteristics or features, namely brightness (B), shape (S) and edge gradients (G). First, separate exterior and interior outline regions are grown as 4-connected neighborhoods around the boundary of the spot (i.e. pixels just within the spot and pixels just outside the spot that touch its boundary by a side of the pixel). The brightness measure (B) is computed as the average intensity of all pixels comprising the spot. To determine the shape measure S, there is first computed the area A of the spot, as the number of pixels comprising the spot, and the perimeter P of the spot, as the greater of the number of pixels comprising the exterior and interior outline regions. The shape measure S (which increases as a shape becomes less compact) is:

$$S=P^2/A$$

The gradient measure G is computed by 1) for each pixel in the exterior and interior outline regions adding the absolute values of the first derivatives in the X and Y directions determined in boxes 26 and 28, as an approximation of gradient magnitude; 2) computing respective averages of these approximate gradient magnitudes for the pixels of the exterior and interior outline regions; and 3) choosing as the gradient measure G, the greater of the averages for these two regions.

The feature measures are relatively weighted to give good results in classifying those spots for which the following inequality is true to be microcalcifications (where ln is natural logarithm):

$$(9 \ln B + 7 \ln G - 2 \ln S) > 100$$

The detection in box 26 of whether the microcalcifications identified in box 22 are isolated or grouped in spatial clusters utilizes two techniques. First, data points identifying the locations of the centroids of the microcalcifications are clustered using the single link hierarchical method. All data points that are contained within an area of less than 1 cm square are grouped together. If the reader is unfamiliar with the mathematics of data clustering, see A. K. Jain et al., "Algorithms for Clustering Data", chapter 3, pp. 72-80, Prentice-Hall, Englewood Cliffs, N.J., 1988. Clusters with fewer than three members are considered to be benign, while clusters with 3 or more members are suspicious for malignant disease. It is the suspect clusters which are, by box 26, indicated in a display of the original image.

While the present invention has been described in particular detail in relation to identification of microcalcifications in mammographic images, it should also be appreciated that its principles have broad general applicability to the identification of spots in radiologic images which correspond to objects associated with malignancy, e.g. lung nodules in chest X-rays. Consequently, numerous modifications are possible in the details given which are within the intended spirit and scope. For example, the radiologic images might be the negative of those discussed with objects producing greater X-ray attenuation than their surround being locally dark.

What is claimed is:

1. A method for aiding detection of cancer, comprising:
    generating a radiologic image of a region of internal human anatomy by detecting radiation exiting from said region, said image comprising a two dimensional array of pixel positions having respective digitized intensity values; storing said image in a digital storage device; and automatically performing the following steps with a computer having access to the storage device:
    computing filtered second spatial derivative of intensity values for pixel positions of the radiologic image, in a manner which preserves the locations of edges of any spots in said image different in intensity from their surrounds as zero crossings in values of said second derivative;
    identifying one or more spots at pixel positions of the radiologic image as a function of the filtered second spatial derivative;
    computing a plurality of measures of features of the identified one or more spots, said plurality of measures being indicative of at least shape and edge gradient of said spots; and
    based on a determination from said measures of features computed, identifying which of said spots correspond to objects of a type associated with malignancy.

2. The cancer detection aiding method as claimed in claim 1, wherein said radiologic image is a mammogram and said objects are microcalcifications, said method further comprising:
    identifying one or more clusters of said spots identified as corresponding to microcalcifications of a type associated with malignancy; and
    providing a human intelligible indication of location in the radiologic image of said identified one or more clusters.

3. The cancer detection aiding method as claimed in claim 1, wherein said filtered second derivative is computed as follows:
    computing first spatial derivative of intensity values at pixel positions in said radiologic image;
    iteratively adaptive smoothing the first spatial derivative values in a manner that an adaptive smoothed first derivative value for a considered pixel position is arrived at by adaptive weighting first derivative values at adjoining pixel positions to achieve a relatively great smoothing effect when such adjoining pixel positions have first spatial derivative values which are relatively similar to the first spatial derivative value of the considered pixel position and to achieve relatively little or no smoothing effect when such adjoining pixel positions have first spatial derivative values which are relatively different from the first spatial derivative value at the considered pixel position; and
    computing spatial derivative values of the adaptive smoothed first spatial derivative values to form filtered second spatial derivative of intensity values.

4. The cancer detection aiding method as claimed in claim 2, wherein said filtered second derivative is computed as follows:
    computing first spatial derivative of intensity values at pixel positions in said radiologic image;
    iteratively adaptive smoothing the first spatial derivative values in a manner that an adaptive smoothed first derivative value for a considered pixel position is arrived at by adaptive weighting first derivative values at adjoining pixel positions to achieve a relatively great smoothing effect when such adjoining pixel positions have first spatial derivative values which are relatively similar to the first spatial derivative value of the considered pixel position and to achieve relatively little or no smoothing effect when such adjoining pixel positions have first spatial derivative values which are relatively different from the first spatial derivative value at the considered pixel position; and
    computing spatial derivative values of the adaptive smoothed first spatial derivative values to form filtered second spatial derivative of intensity values.

* * * * *